(12) United States Patent
Davé et al.

(10) Patent No.: US 7,785,615 B2
(45) Date of Patent: Aug. 31, 2010

(54) BIODEGRADABLE MEDICAL IMPLANT WITH ENCAPSULATED BUFFERING AGENT

(75) Inventors: Vipul Bhupendra Davé, Hillsborough, NJ (US); George Landau, Verona, NJ (US); Premal Patel, Plainsboro, NJ (US)

(73) Assignee: Cordis Corporation, Miami Lakes, FL (US)

( * ) Notice: Subject to any disclaimer, the term of this patent is extended or adjusted under 35 U.S.C. 154(b) by 1081 days.

(21) Appl. No.: 10/856,462

(22) Filed: May 28, 2004

(65) Prior Publication Data

US 2005/0267565 A1     Dec. 1, 2005

(51) Int. Cl.
 *A61F 2/00*     (2006.01)
(52) U.S. Cl. .................. 424/423; 514/772; 424/422
(58) Field of Classification Search ............... None
 See application file for complete search history.

(56) References Cited

U.S. PATENT DOCUMENTS

| | | | |
|---|---|---|---|
| 4,619,655 A | 10/1986 | Hanker et al. | |
| 5,290,271 A | 3/1994 | Jernberg | |
| 5,338,772 A | 8/1994 | Bauer et al. | |
| 5,543,158 A * | 8/1996 | Gref et al. .................. | 424/501 |
| 5,629,077 A | 5/1997 | Turnlund et al. | |
| 5,679,723 A | 10/1997 | Cooper et al. | |
| 5,766,710 A | 6/1998 | Turnlund et al. | |
| 5,817,328 A | 10/1998 | Gresser et al. | |
| 5,885,797 A | 3/1999 | Chen et al. | |
| 5,935,769 A | 8/1999 | Tsukada | |
| 5,981,568 A | 11/1999 | Kunz et al. | |
| 6,206,931 B1 | 3/2001 | Cook et al. | |
| 6,228,111 B1 | 5/2001 | Tormala et al. | |
| 6,258,121 B1 * | 7/2001 | Yang et al. .................. | 623/1.46 |

(Continued)

FOREIGN PATENT DOCUMENTS

WO     WO 96/19248 A2     6/1996

OTHER PUBLICATIONS

Acuna, V. et al. Composites of Lactic Acid Polymer and Calcium Phosphate or Calcium Carbonate as Degradable Bone Fillers, 1992, Advances in Biomaterials, Elsevier, Amsterdam, NL, pp. 391-398.

(Continued)

*Primary Examiner*—Eric E. Silverman
(74) *Attorney, Agent, or Firm*—Louis J. Capezzuto

(57) ABSTRACT

A medical device for placement at a site in a patient's body and for controlling pH levels at the site in the patient's body includes one or more structural components made of a first biodegradable and/or bioabsorbable material or, alternatively, one or more structural components having a coating thereon made of a first biodegradable and/or bioabsorbable material. The device also includes a buffering agent and at least one second biodegradable and/or bioabsorbable material on or in the one or more structural components, or alternatively, on or in the coating on the one or more structural components. The at least one second biodegradable and/or bioabsorbable material encapsulates the buffering agent and the buffering agent is dispersed from the at least one second biodegradable and/or bioabsorbable material in response to hydrolysis of the first biodegradable and/or bioabsorbable material. Additionally, the device can include a drug that is either also encapsulated by the at least one second biodegradable and/or bioabsorbable material or is included with the first biodegradable and/or bioabsorbable material.

44 Claims, 4 Drawing Sheets

U.S. PATENT DOCUMENTS

| | | |
|---|---|---|
| 6,358,989 B1 | 3/2002 | Kunz et al. |
| 6,383,519 B1 | 5/2002 | Sapieszko et al. |
| 6,419,945 B1 | 7/2002 | Gresser et al. |
| 6,491,666 B1 | 12/2002 | Santini, Jr. et al. |
| 6,548,002 B2 | 4/2003 | Gresser et al. |
| 6,626,950 B2 | 9/2003 | Brown et al. |
| 6,720,350 B2 | 4/2004 | Kunz et al. |
| 6,913,765 B2 | 7/2005 | Li et al. |
| 7,041,657 B2 | 5/2006 | Vournakis et al. |
| 7,115,588 B2 | 10/2006 | Vournakis et al. |
| 2002/0054914 A1 | 5/2002 | Morcol et al. |
| 2002/0143403 A1 | 10/2002 | Vaidyanathan et al. |
| 2003/0041386 A1 | 3/2003 | Cook et al. |
| 2004/0158194 A1 | 8/2004 | Wolff et al. |
| 2005/0123588 A1 | 6/2005 | Zhu et al. |
| 2005/0256069 A1 | 11/2005 | Manoharan et al. |
| 2005/0267565 A1 | 12/2005 | Dave et al. |
| 2005/0278015 A1 | 12/2005 | Dave et al. |
| 2005/0281781 A1 | 12/2005 | Ostroff |
| 2008/0086199 A1 | 4/2008 | Dave et al. |
| 2008/0167727 A1 | 7/2008 | Cook et al. |
| 2008/0167728 A1 | 7/2008 | Cook et al. |
| 2008/0171092 A1 | 7/2008 | Cook et al. |
| 2008/0268045 A1 | 10/2008 | Dervieux |
| 2009/0017558 A1 | 1/2009 | Weisgraber et al. |

OTHER PUBLICATIONS

Agrawal, C.M. et al. Technique to Control PH in Vicinity of Biodegrading PLA-PGA Implants, 1997 John Wiley & Sons, Inc. CCC 0021-9304/97/020105-10. J. Biomed Mater Res (Appl Biomater) 38:105-114, 1997.

Bostman et al. Biodegradable Internal Fixation for Malleolar Fractrures, British Editorial Society of Bone and Joint Surgery, 69-B(4) 615-619 (1987).

Bostman et al. Ankle Fractures Treated Using Biodegradable Internal Fixation, Clinical Orthopedic 238, 195-203 (1989).

Bostman et al. Degradable Polyglycolide Rods for the Internal Fixation of Displaced Bimalleolar Fractures, International Orthopedic 14, 1-8 (1990).

Bostman et al. Current Concepts Review Absorbable Implants for the Fixation of Fractures, Joint Bone and Joint Surgery, 73, 148-153 (1991).

Hirvensalo et al. Biodegradable Fixation in Intraarticular Fractures of the Elbow Joint, Acta Orthop. Scandinavica, Supplementum 227, 78-79 (1988).

Hoffmann et al. Die Distale Radiusfraktur. Frakturstabilisierung Mit Biodegradablen Osteosynthese-Stiften (Biofix, Die Versorgung Von Sprunggelenlzsfrakturen Unter Verwendung Von Platten Und Schrauben Aus Resorbserbarem Polymermaterial, Jahrestagung der Deutschen Gesellschaft fur Unfallheikunde, Berlin, Nov. 22, 1989 92:430-434 with English Summary.

Partio et al. Total Arthroplasties of the Knee in Middle-Finland Central Hospital Between 1977 and 1984, Acta Orthop. Scandinavica, Supplementum 235 61 (1) 43-44 (1990).

Rokkanen et al. Biodegradable Implants in Fracture Fixation: Early Results of Treatment of Fractures of the Ankle, Lancet 1, 1422-1425 (1985).

Schiller, C. et al. Carbonated Calcium Phosphates are Suitable PH-Stabilising Fillers for Biodegradable Polyesters, 2003 Elsevier Science Ltd., Biomaterials 24 (2003) 2037-2043.

Schiller, C. et al. Geometrically Structured Implants for Cranial Reconstruction Made of Biodegradable Polyesters and Calcium Phosphate/Calcium Carbonate, Mar. 2004 Biomaterials, Elseviercience Publishers BV., Baring, GB, pp. 1239-1247.

Vert et al. More About the Degradation of LA/GA-Derived Matrices in Aqueous Media, J. Controlled Release 16, 15-26 (1991).

European Search Report EP 05 25 3317 dated Sep. 6, 2005.

BE.462J/3.962J (Spring 2004).

Kwon, Ick Chan et al., Electrically Erodible Polymer Gel for Controlled Release of Drugs, Letters to Nature, Nov. 28, 1991, pp. 291-293, vol. 354, Nature Publishing Group.

U.S. Office Action dated Nov. 24, 2009 issued in related U.S. Appl. No. 10/856,459.

U.S. Office Action dated Apr. 29, 2009 issued in related U.S. Appl. No. 10/856,459.

U.S. Office Action dated Nov. 17, 2008 issued in related U.S. Appl. No. 10/856,459.

U.S. Office Action dated Apr. 8, 2008 issued in related U.S. Appl. No. 10/856,459.

U.S. Office Action dated Jul. 16, 2007 issued in related U.S. Appl. No. 10/856,459.

U.S. Office Action dated Nov. 16, 2006 issued in related U.S. Appl. No. 10/856,459.

* cited by examiner

BIODEGRADABLE MEDICAL IMPLANT WITH ENCAPSULATED BUFFERING AGENT

FIELD AND BACKGROUND OF THE INVENTION

The present invention relates, in general, to implantable medical devices, and, in particular, to new and useful bioabsorbable medical devices that are capable of being a self-regulating system for controlling the acidic effects of degradation. Additionally, the present invention relates, in particular, to bioabsorbable medical devices for vascular or cardiovascular applications that can control the acidic effects of degradation.

Bioabsorbable implants are typically made from polymeric materials such as lactone-based polyesters. These bulk eroding materials breakdown over time due to chemical hydrolysis to produce water-soluble, low molecular weight fragments. These fragments are then attacked by enzymes to produce lower molecular weight metabolites. Acid fragments that are produced during degradation of the polymer backbone have shown to cause local tissue inflammation. The inflammation has been observed in vascular systems as well and the extent of inflammation depends on the pH of the acid that in turn is dependent on the type and amount of acid produced during degradation. This inflammation is not typically observed in polymers that degrade by surface erosion (such as polyorthoesters and polyanhydrides) as the amount of acid released at a given time is small to cause tissue inflammation.

Additionally, most of the past research in the field of bioabsorbable implants has been directed toward orthopedic applications, for instance, toward using a bioabsorbable implant as internal fixation devices in bone. Thus, this trend is specifically toward internal fixation devices for repair of damaged bone through the use of resorbable, tissue compatible biopolymers. Biopolymers such as poly(glycolic acid) [PGA], poly(lactide) [PLA], and copolymers of lactic and glycolic acids, [poly(lactide-co-glycolide) or PLGA] have been used in the production of internal fixation devices, such as screws, pins, and rods to hold bone together following surgery, or to repair broken bones. Other polymers, such as poly(dioxanone), have also been considered for use in the manufacture of surgical internal fixation devices. However, it has been observed that tissue response to resorbable implants fabricated from these biopolymers is not uniformly acceptable (Bostman, J. Bone and Joint Surg. 73, 148-153 (1991).

The tissue response to these biopolymer-based orthopedic implants has been well documented. Late sterile inflammatory foreign body response (sterile abscess) has been reported in about 8% of fractures repaired with these polymers (Bostman, supra). In a randomized study of 56 open reduction and internal fixation of malleolar fractures of the ankle with metal ASIF screws and plates or with rods of PLGA, two cases of sterile inflammatory wound sinus were observed 3 to 4 months after the operation in the injuries fixed with the polymer rods (Rokkanen et al., Lancet 1, 1422-1425 (1985); Bostman et al., J. Bone and Joint Surg., 69-B(4), 615-619 (1987)).

Other orthopedic studies have also documented an inflammatory reaction following implantation of PGA or PLGA orthopedic fixation devices. The fraction of patients suffering from this reaction ranges from 4.6 to 22.5% (Bostman et al., Clin. Orthop. 238, 195-203 (1989); Bostman et al., Internat. Orthop. 14, 1-8 (1990); Hirvensalo et al., Acta Orthop. Scandinavica, Supplementum 227, 78-79 (1988); Hoffman et al., Unfallchirurgie 92, 430-434 (1989); Partio et al., Acta Orthop. Scandinavica, Supplementum 237, 43-44 (1990); Bostman et al., Internat. Orthop. 14, 1-8 (1990)).

Moreover, the inflammatory reaction is not limited to orthopedic implants made from poly(glycolide) polymers. Internal fixation devices made from poly(lactide) have also been observed to exhibit an inflammatory reaction. Eitenmuller et al. reports that 9 of 19 patients (47.7%) who had fractures of the ankle treated with absorbable plates and screws of poly(lactide) had an inflammatory response. (J. Eitenmuller, A. David, A. Pomoner, and G. Muhyr: "Die Versorgung von Sprunggelenlzsfrakturen unter Verwendung von Platten und Schrauben aus resorbserbarem Polymermaterial", Read at Jahrestagung der Deutschen Gesellschaft fur Unfallheilkunde, Berlin, Nov. 22, 1989).

Additionally, in vitro studies have been performed to monitor pH changes as well as weight loss and the appearance of lactic acid from orthopedic screws fabricated from poly(lactide-co-glycolide) with a lactide:glycolide ratio of 85:15. (Vert et al., J. Controlled Release 16, 15-26 (1991)). An induction period of about ten weeks was observed before any significant change in media pH or weight loss occurred. This time period corresponds to the induction periods of seven to twenty weeks noted by orthopedic clinicians. However, no attempt had been made to alleviate the source of inflammation.

One known in vitro study involving orthopedic implants is described in J Biomed Mater Res (Appl Biomater) 38: 105-114, 1997 and was performed to examine if the pH decrease in the vicinity of degrading polylactic acid (PLA) and polyglycolic acid (PGA) polymers could be offset by incorporation of basic salts within PLA-PGA orthopedic implants. It had been suggested that such pH lowering results in adverse effects, which may be responsible for biocompatibility concerns raised recently about PLA and PGA polymers. Accordingly, this study was conducted and the results indicated that all three salts investigated in this study were successful in controlling the decrease in pH due to the acidic degradation products of the copolymer. The pH of the test media for the control group fell to a value of 3.0 at 9 weeks. Implants containing calcium carbonate maintained the pH value between 7.4 and 6.3 throughout the degradation process. Implants with calcium hydroxyapatite and sodium bicarbonate controlled the pH values between 6.9 and 4.3 and 8.2 and 4.5, respectively. At 3 weeks, marked swelling of implants containing calcium carbonate or sodium bicarbonate was observed relative to the control orthopedic implants. The molecular weight and mass changes in the orthopedic implants did not show any significant differences at 9 weeks. Thus, results from this in vitro study showed that a significant decrease in pH in the vicinity of a PLA-PGA orthopedic implant could be avoided by incorporating basic salts into the orthopedic implant itself.

To date, there have been no known bioabsorbable medical devices that are capable of being a self-regulating system for controlling the acidic effects of degradation. Additionally, to date, there have been no known bioabsorbable medical devices for vascular or cardiovascular applications that can control the acidic effects of degradation.

SUMMARY OF THE INVENTION

The present invention relates to medical devices that are placed or implanted in the body including medical devices that are placed in vessels such as an artery or a vein or ducts or organs such as the heart. Particularly, the present invention is a medical device that is either made of biodegradable and/or bioabsorbable material or is coated with biodegradable and/or bioabsorbable material for helping to suppress inflammation and the effects of inflammation and, in some embodiments, for efficaciously delivering a therapeutic agent.

The present invention is a biodegradable and/or bioabsorbable medical device for placement or implantation in a patient's body, wherein the medical device is a self-regulating system for controlling the acidic effects of degradation. Additionally, the biodegradable and/or bioabsorbable medical device in accordance with the present invention is a device designed for placement within a vessel or duct, and more particularly, vasculature such as an artery or vein, as well as for placement on, within or into an organ, and more particularly, a portion of the heart and can control the acidic effects of degradation. Even more particularly, the present invention is a medical device that is a device for vascular or cardiovascular use such as a stent or valve can control the acidic effects of degradation.

In some embodiments, the present invention is a medical device for placement at a site in a patient's body and for controlling pH levels at the site in the patient's body and comprises one or more structural components made of a first biodegradable and/or bioabsorbable material or, alternatively, one or more structural components having a coating thereon made of a first biodegradable and/or bioabsorbable material. The device also comprises a buffering agent and at least one second biodegradable and/or bioabsorbable material on or in the one or more structural components, or alternatively, on or in the coating on the one or more structural components. The at least one second biodegradable and/or bioabsorbable material encapsulates the buffering agent and the buffering agent is dispersed from the at least one second biodegradable and/or bioabsorbable material in response to hydrolysis of the first biodegradable and/or bioabsorbable material. Additionally, the device can include a drug that is either also encapsulated by the at least one second biodegradable and/or bioabsorbable material or is included with the first biodegradable and/or bioabsorbable material.

In other embodiments, the present invention is a vascular or cardiovascular medical device for placement at a site in a patient's body and for controlling pH levels at the site in the patient's body and comprises one or more structural components made of a biodegradable and/or bioabsorbable material, or alternatively, a coating thereon made of a biodegradable and/or bioabsorbable material. A buffering agent is provided on or in the biodegradable and/or bioabsorbable material and the buffering agent is dispersed from the biodegradable and/or bioabsorbable material in response to hydrolysis of the biodegradable and/or bioabsorbable material. Additionally, the vascular or cardiovascular medical device can include a drug that is included with the biodegradable and/or bioabsorbable material. The vascular or cardiovascular medical device can also be a stent or a valve.

BRIEF DESCRIPTION OF THE DRAWINGS

The novel features of the invention are set forth with particularity in the appended claims. The invention itself, however, both as to organization and methods of operation, together with further objects and advantages thereof, may be understood by reference to the following description, taken in conjunction with the accompanying drawings in which:

DESCRIPTION OF THE PREFERRED EMBODIMENTS

Figure 1:
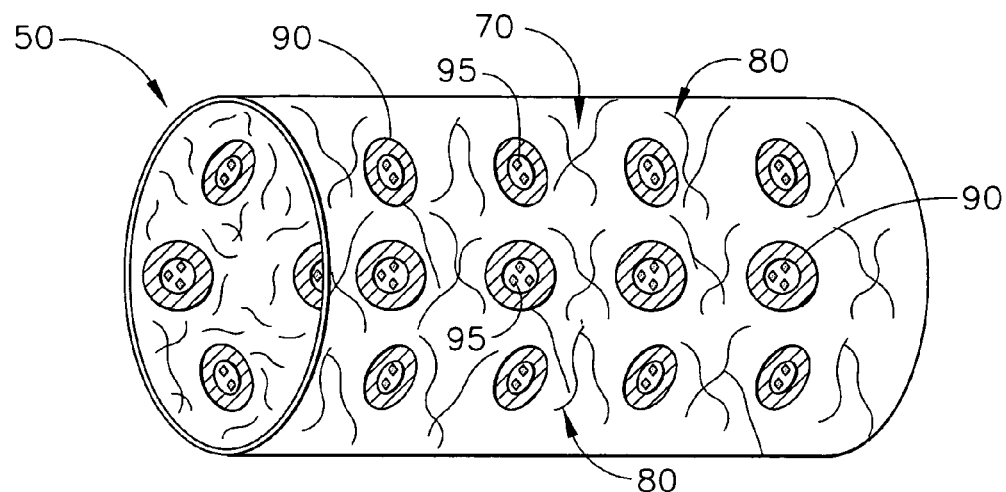
FIG. 1 is a schematic illustration of a medical device having a first biodegradable and/or bioabsorbable material and a second biodegradable and/or bioabsorbable material, shown as a cross-sectional slice taken from a sphere, whose degradation is triggered by degradation products produced by degrading of the first biodegradable and/or bioabsorbable material in accordance with the present invention.

The present invention relates to medical devices that are placed or implanted in the body including medical devices that are placed in vessels such as an artery or a vein or ducts or organs such as the heart. Particularly, the present invention is a medical device that is either made of bioabsorbable material or is coated with bioabsorbable material for helping to suppress inflammation and the effects of inflammation and, in some embodiments, for efficaciously delivering a therapeutic agent.

As used herein, the terms "biodegradable", "degradable", "degradation", "degraded", "bioerodible", "erodible" or "erosion" are used interchangeably and are defined as the breaking down or the susceptibility of a material or component to break down or be broken into products, byproducts, components or subcomponents over time such as days, weeks, months or years.

As used herein, the terms "bioabsorbable", "absorbable", "resorbable" and "bioresorbable" are used interchangeably and are defined as the biologic elimination of any of the products of degradation by metabolism and/or excretion.

As used herein, the terms "buffering agent", "buffering compound", "buffer", "neutralizing agent", "neutralizing compound", "neutralization agent", or "neutralization compound" are used interchangeably and defined as any material, agent, compound or substance that limits or moderates the rate of change of the pH of a medical device or the local or near environment of the medical devices upon exposure to acid or base.

As used herein, the term "acid", "acid components", "acid products", "acid byproducts", "acidic", "acidic products", "acidic components" or "acidic byproducts" are used interchangeably and are defined as any product that generates an aqueous solution or environment with a pH less than 7.

As used herein, the term "composite", "biodegradable material", "biodegradable polymer", "bioabsorbable material", "bioabsorbable polymer" "biodegradable and/or bioabsorbable material" or "biodegradable and/or bioabsorbable polymer" are used interchangeably and are defined as any polymer material that is biodegradable or bioabsorbable in the body.

As used herein, the terms "agent", "therapeutic agent", "active agent", "drug", "active drug", and "pharmaceutical agent" are used interchangeably herein and define an agent, drug, compound, composition of matter or mixture thereof which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, blood pressure medications and cholesterol lowering agents including statins, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of the therapeutic agents or drugs 99 useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chiormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, atorvastatin, simvastatin, pravastatin, fluvastatin, lovastatin, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

Moreover, drugs or pharmaceutical agents 99 useful for the medical device 50 include: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)I-$I_b III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoietin, angiotensin receptor blocker; nitric oxide donors; anti-sense oligionucleotides and combinations thereof, cell cycle inhibitors, mTOR inhibitors, growth factor signal transduction kinase inhibitors, chemical compound, biological molecule, nucleic acids such as DNA and RNA, amino acids, peptide, protein or combinations thereof.

It is to be understood that the use of the term "agent", "therapeutic agent", "active agent", "drug", "active drug", and "pharmaceutical agent" includes all derivatives, analogs and salts thereof and in no way excludes the use of two or more such agents, therapeutic agents, active agents, drugs, active drugs, or pharmaceutical agents.

Referring now to FIG. 1, the present invention is a biodegradable and/or bioabsorbable medical device, generally designated 50, for placement or implantation in a patient's body, wherein the medical device 50 is a self-regulating system for controlling the acidic effects of degradation. Additionally, biodegradable and/or bioabsorbable medical device 50 is a device designed for placement within a vessel or duct, and more particularly, vasculature such as an artery or vein, as well as for placement on, within or into an organ, and more particularly, a portion of the heart and can control the acidic effects of degradation. Even more particularly, the present invention is a medical device 50 that is a device for vascular or cardiovascular use such as a stent or valve can control the acidic effects of degradation.

Although medical device 50 is not limited to any particular configuration, in certain embodiments according to the present invention, medical device 50 has a substantially cylindrical configuration and is substantially hollow along its longitudinal axis and terminates at an open end at each end of its cylindrical configuration. Accordingly, the configuration of medical device 50 in accordance with the present invention and as described above is best suited as a stent for placement within a vessel for treatment of cardiovascular disease such as stenosis, artherosclerosis, vulnerable plaque, or ischemic heart disease or as a valve such as a heart valve for regulating blood flow.

Medical device 50 has structure, features and components 70 that optionally include hoops, loops, flexible links or bridges or extensions (not shown) that are either made of a first bioabsorbable material 80 itself or that are coated with a first biodegradable and/or bioabsorbable material 80, i.e. serves as a coating 70 having a first biodegradable and/or bioabsorbable material 80.

Medical device 50 is a self-regulating biodegradable and/or bioabsorbable system having a selective mechanism to control the undesirable effects from the degradation or erosion of any biodegradable and/or bioabsorbable material used for the device 50 such as the degradation products and acid produced therefrom or from any acidic byproducts produced by the degradation of the biodegradable and/or bioabsorbable material.

The first biodegradable and/or bioabsorbable material 80 is used as the base material for structural aspects 70 of the device 50 such as hoops, loops, flexible links or bridges or extensions of the stent 50 or the housing, flaps or other components 70 of the heart valve 50. When applied as a coating 70, the first biodegradable and/or bioabsorbable material 80 is used as the coating material 70 to be coated over the structural aspects of the device or stent 50 such as hoops, loops, flexible links or bridges or extensions of the stent 50 or the housing, flaps or other components of the heart valve 50.

The first biodegradable and/or bioabsorbable material 80 is a bulk erodible polymer (either a homopolymer, copolymer or blend of polymers) such as any one of the polyesters belonging to the poly(alpha-hydroxy acids) group. This includes aliphatic polyesters such poly (lactic acid); poly (glycolic acid); poly (caprolactone); poly (p-dioxanone) and poly (trimethylene carbonate); and their copolymers and blends. Other polymers useful as the first bioabsorbable material include amino acid derived polymers [e.g., poly(iminocarbonates)]; phosphorous containing polymers [e.g., poly (phosphazenes); poly (phosphoesters)] and poly (ester amide).

The rate of hydrolysis of the first biodegradable and/or bioabsorbable material 80 depends on the type of monomer used to prepare the bulk erodible polymer. For example, the absorption times (time to complete degradation or fully degrade) are estimated as follows: poly(caprolactone) and poly (trimethylene carbonate) takes more than 3 years; poly (lactic acid) takes about 2 years; poly(dioxanone) takes about 7 months; and poly (glycolic acid) takes about 3 months.

Absorption rates for copolymers prepared from the monomers such as poly(lactic acid-co-glycolic acid); poly(glycolic acid-co-caprolactone); and poly(glycolic acid-co-trimethylene carbonate) depend on the molar amounts of the monomers. The degradation of the polymers is by hydrolysis and the byproducts are typically water soluble fragments such as monomers that are used to prepare the polymers [for example, lactic acid from poly(lactic acid); glycolic acid from poly (glycolic acid)] which are metabolized by enzymatic attack then enters the kreb's cycle and excreted as carbon dioxide and water. pH values can vary based on the type and amount of acid. If the polymer 80 absorbs slowly, then the pH values will be high as there is less amount of acid and vice versa. For example, high amount of lactic acid at a given time can have pH between 2 to 4.

Figure 2:
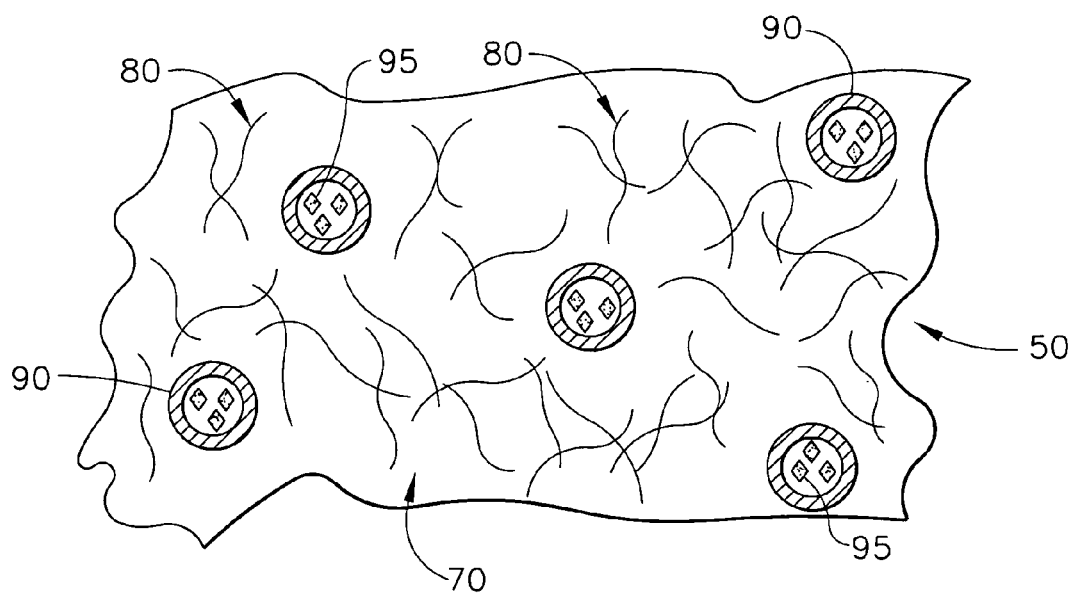
FIG. 2 is a schematic illustration of a portion of structure or coating that can be used for the medical device of FIG. 1 wherein the structure or coating has a second biodegradable and/or bioabsorbable material, shown as a cross-sectional slice taken from a sphere, encapsulating a buffering agent in accordance with the present invention.
Figure 3:
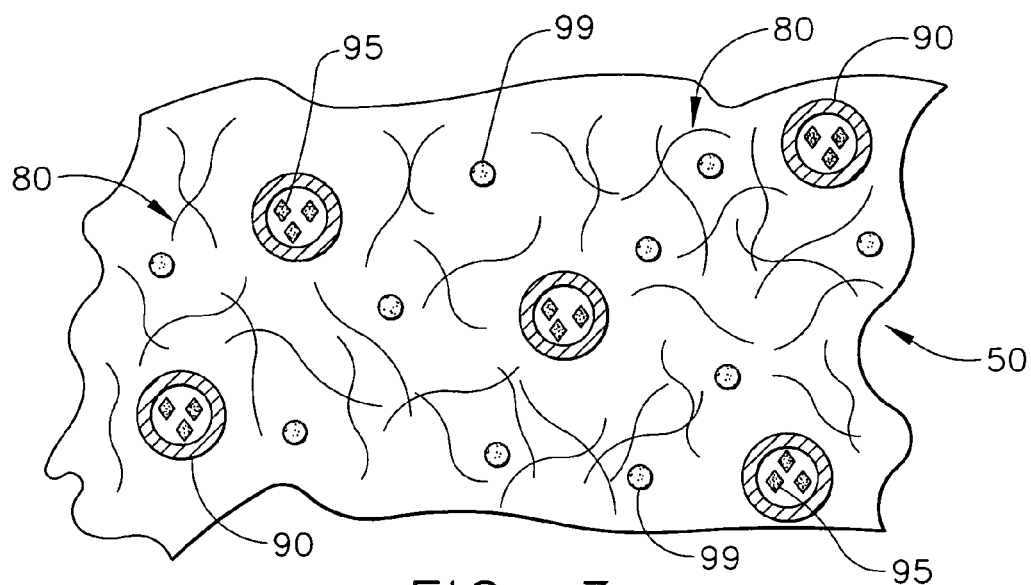
FIG. 3 is a schematic illustration of a portion of structure or coating that can be used for the medical device of FIG. 1 wherein the structure or coating includes a drug and has a second biodegradable and/or bioabsorbable material, shown as a cross-sectional slice taken from a sphere, encapsulating a buffering agent in accordance with the present invention.
Figure 4:
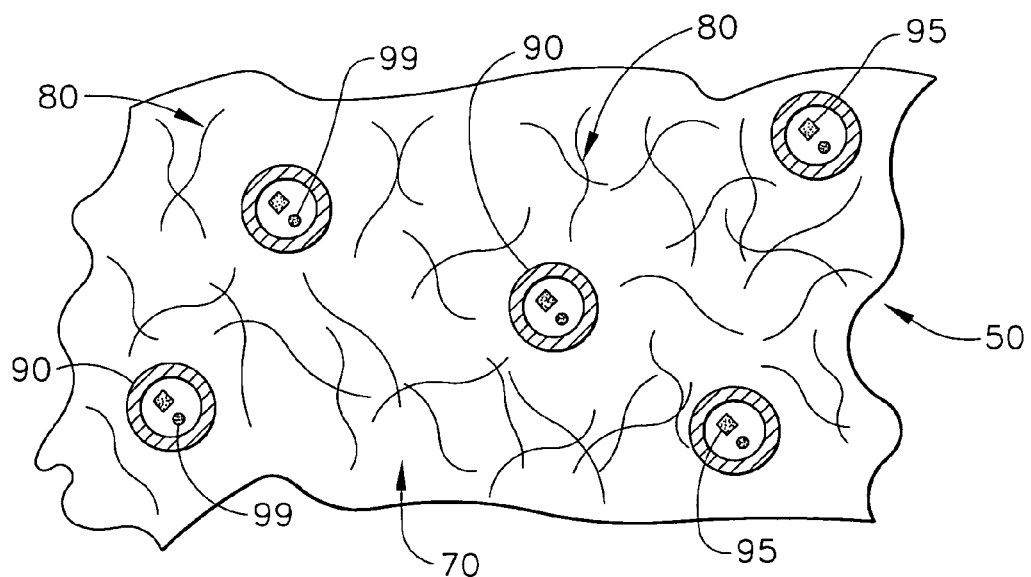
FIG. 4 is a schematic illustration of a portion of structure or coating that can be used for the medical device of FIG. 1 wherein the structure or coating has a second biodegradable and/or bioabsorbable material, shown as a cross-sectional slice taken from a sphere, encapsulating both a buffering agent and a drug in accordance with the present invention.

As shown in FIGS. 1-4, a second biodegradable and/or bioabsorbable material 90 is used to encapsulate (shown as a cross-sectional slice taken from a sphere) a buffering agent or a neutralizing agent 95 (represented by a solid diamond shape). As best illustrated in FIGS. 2-4, the second biodegradable and/or bioabsorbable material 90 is either a surface erodible polymer or a bulk erodible polymer that is reactive to the degradation and acidic environment or acid or inflammatory effects caused from the byproducts (or characteristics of byproducts) from the breakdown of the first biodegradable and/or bioabsorbable material 80. The second biodegradable and/or bioabsorbable material 90 is either a homopolymer or copolymer or blend of polymers selected from a family of polymers that are easily degraded by acid and can include polysaccharides (e.g., cellulose and their derivatives; starch and their derivatives; chitin; chitosan; etc) proteins and polypeptides (e.g., collagen) water soluble polymers; PEG based copolymers; poly(orthoesters); etc.

Accordingly, the second biodegradable and/or bioabsorbable material 90 acts as a selective mechanism or triggering mechanism for releasing the buffering agent 95 from its protected environments or encapsulated state. Thus, an acidic environment caused by inflammation and degradation byproducts of the first biodegradable and/or bioabsorbable material 80 causes or triggers degradation of the second biodegradable and/or bioabsorbable material 90, which in turn, releases the buffering agent 95 into the local area or local environment of the medical device 50 to offset the unwanted effects on tissue (such as the inflammatory effects) or materials near the medical device 50. Thus, the second biodegradable and/or bioabsorbable material 90 (as a microparticle or nanoparticle encapsulating the buffering agent 95 in some embodiments according to the present invention) regulates or controls the local acidic environment at the medical device 50. The components or byproducts produced by degradation of the second biodegradable and/or bioabsorbable material 90, if prepared from polysaccharide, will produce low molecular weight saccharide units and if prepared from proteins will produce amino acids as their byproducts respectively.

The encapsulation of the buffering agent 95 (FIG. 2 and FIG. 3) or the buffering agent 95 and drug 99 (FIG. 4) (represented by a solid circular shape) can be in the form of microparticles or nanoparticles that do not adversely affect the physical properties of the device 50. One embodiment according to the present invention, is to encapsulate the buffering agent 95 or buffering agent 95 and drug 99 (FIG. 4) in a second biodegradable and/or bioabsorbable material 90 whose rate of degradation is either dependent upon the rate of hydrolysis or break down of the first polymer 80 or is dependent upon the level of acidity or acid levels in the local environment. As the first polymer 80 degrades and releases acid, the second polymer 90 degrades and releases the buffering agent 95 (and drug 99 in the embodiment of FIG. 4) to offset the pH of the acid produced from the first polymer 80.

Different types of buffering agents 95 can be used such as inorganic basic fillers. Some examples of these basic compounds include calcium hydroxyapatite; carbonated apatite; tricalcium phosphate; calcium carbonate; sodium bicarbonate; calcium phosphates; carbonated calcium phosphates; and magnesium hydroxide. Also, acid/based titrating compounds (amine monomers); and lactate dehydrogenase (it will convert lactate in to pyruvate which is the end product of glycolysis and starting component of Citric acid cycle) can also be used as the buffering agent 95.

The inorganic fillers 95 will react with the acid, and neutralize the acid that is formed during the absorption of the polymers, e.g. the first biodegradable and/or bioabsorbable material 80 and the second biodegradable and/or bioabsorbable material 90. So, they behave as the buffering agents and prevent the acid content in the immediate environment to be maintained at pH ranging from about 5 to about 7 and more preferably at pH ranging from about 6 to about 7.4. The total amount of inorganic filler or buffering agent 95 should be sufficient to neutralize the total amount of acid that is generated during the absorption process. For example, 1 mole of calcium carbonate is needed to react with 2 mol of lactic acid (see below):

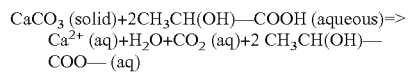

Moreover, the self-regulating system 50 in accordance with the present invention, provides for a stoichiometric balance between the buffering agent 95 and the total amount of acid released from the device 50 (due to degradation of the first biodegradable and/or bioabsorbable polymer 80 and the second biodegradable and/or bioabsorbable polymer 90 if applicable). Furthermore, the device 50 can be fabricated in such a way that will allow for homogenous or preferential distribution (e.g., layers) of the buffering agent so that there will be good control of the self-regulating system.

Figure 7:
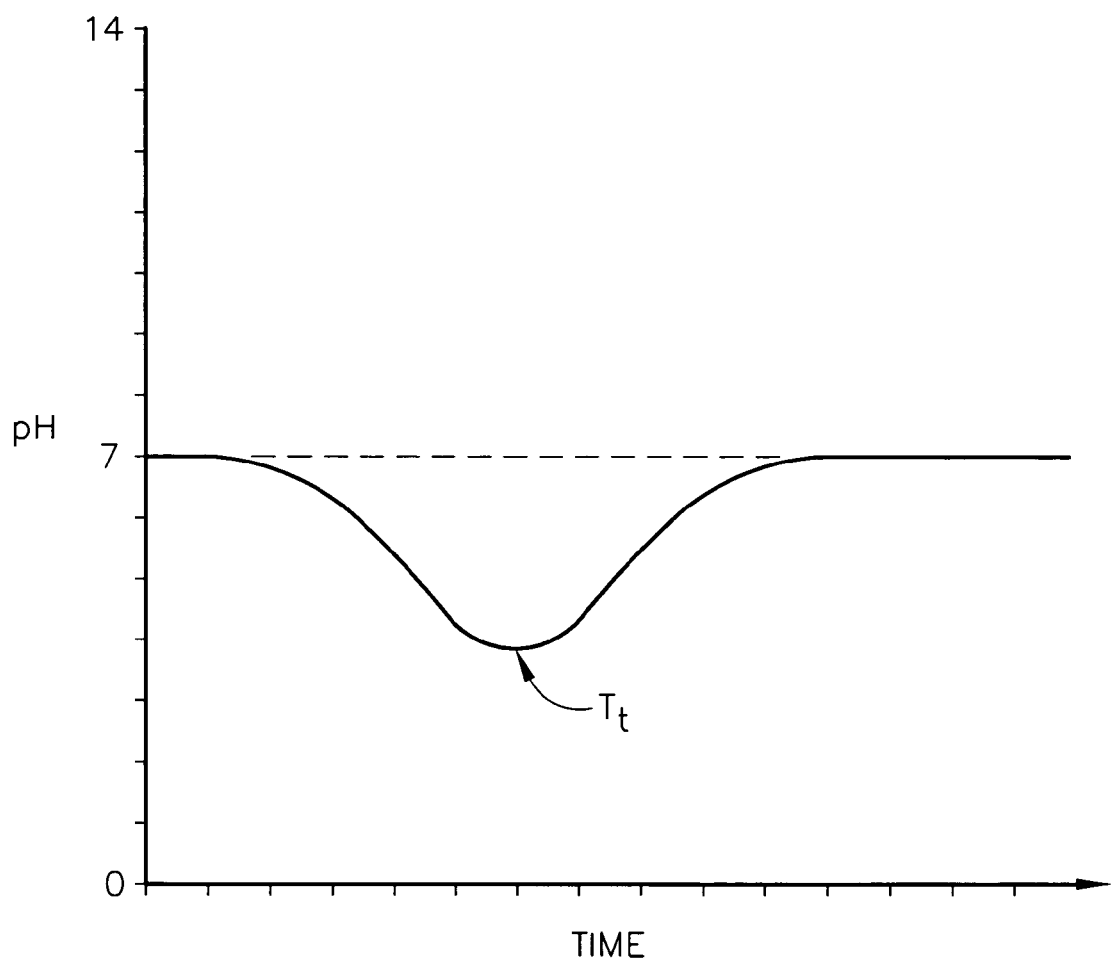
FIG. 7 is a graph illustrating pH levels over time based on degradation of the medical device of FIG. 1 in accordance with the present invention.

A typical representation of the pH control and modulation as a function of time of the self-regulating system provided by the medical device 50 in accordance with the present invention is represented in FIG. 7. The ideal pH of about 7 (normal blood pH is about 7.4) is preferable as it is neutral and will not cause any tissue inflammation (represented by a horizontal, dashed line). When the pH begins to drop (e.g., pH of about 4 in one embodiment according to the present invention) due to the acid released from polymer degradation of polymer 80, the buffering agent 95 is released and raises the pH back to 7, i.e. to about 7.4. The trigger (triggering time $T_t$) to release the buffering agent can be at different pH (for example, in other embodiments according to the present invention, pH ranging from about 3 to about 6) so that at a given time, the pH of the system 50 never drops to a level sufficient to cause or induce inflammation.

As best depicted and represented in FIG. 7, a graph is used to illustrate the biodegradable action and effects attributed to the medical device 50 in accordance with the present invention. Particularly, FIG. 7 illustrates pH levels over time based on degradation of the medical device 50 (FIG. 1) after placement or implantation of the device 50 in a patient's body, for instance, after the stent 50 is deployed in a vessel in accordance with the present invention.

Ideally, it is desirable to maintain a neutral pH level, i.e. pH of about 7 (normal blood pH is about 7.4) (represented by horizontal, dashed line) or whatever the pH level was prior to placement of the device 50 in the tissue to be treated. As the first biodegradable and/or bioabsorbable material 80 degrades over time, acidic byproducts are formed and resulting inflammation is known to occur as a result as indicated by the solid line declining over time representing lower pH (increasing acidic environment in the local area of the device 50), the encapsulation material 90 (FIGS. 1, 2, 3, and 4) will hydrolyze at a triggering time $T_t$ by acid hydrolysis and release the buffering agent 95 into the local environment around the device 50.

Thus, the present invention is a medical device 50 that is self-regulating system that provides control or reduction of the inflammation caused by biodegradable and/or bioabsorbable polymers 80 and 90 (FIG. 1, FIG. 2, FIG. 3, and FIG. 4) that degrades by bulk erosion and surface erosion respectively that can be used as coatings 70 for metal stent 50 and as biodegradable and/or bioabsorbable polymer stent 50 (stent made entirely of biodegradable and/or bioabsorbable material) that are implanted or deployed in vascular systems. The encapsulation can be micro particles or nano particles that do not adversely affect the physical properties of the device. One embodiment would be to encapsulate a buffering agent in a second biodegradable and/or bioabsorbable material whose rate of degradation is either dependent upon the rate of break down of the first polymer or is dependent upon the level of acidity. As the first polymer degrades and releases acid, the second polymer degrades and releases a buffering agent to offset the pH of the acid from the first polymer. A typical representation of the pH control and modulation as a function of time is represented in FIG. 7. The ideal pH of about 7 (7.4 for normal blood) is preferable as it is neutral and will not cause any tissue inflammation. When the pH begins to drop (e.g., 5) due to the acid released from polymer degradation, the buffering agent is released and raises the pH back to 7 and preferably pH at about 7.4. The trigger to release the buffering agent can be at different pH (3 to 6) so that at a given time, the pH of the system never drops to cause inflammation. There should be a stoichiometric balance between the buffering agent and the total amount of acid released from the device. The device can be fabricated in such a way that will allow homogenous or preferential distribution (e.g., layers) of the buffering agent so that there will be good control of the self-regulating system.

In a three component or four component system (FIG. 1, FIG. 2, FIG. 3 and FIG. 4), i.e. first polymer 80, second polymer 90 encapsulating the buffering agent 95 and optionally the drug 99 respectively, the three components or four components (when including drug 99) are formulated together to create an effective self-regulating system. As the first polymer material 80 breaks down the second polymer material 90 reacts/degrades and releases the encapsulated buffering agent 95 (and the drug 99 in the embodiment of FIG. 4) which offset the unwanted effects of acid and inflammation. If the first polymer material 80 breaks down quickly, the buffering agent 95 is released faster (and vice-versa) to maintain a level of control on the degradation kinetics of the device 50.

Figure 5:
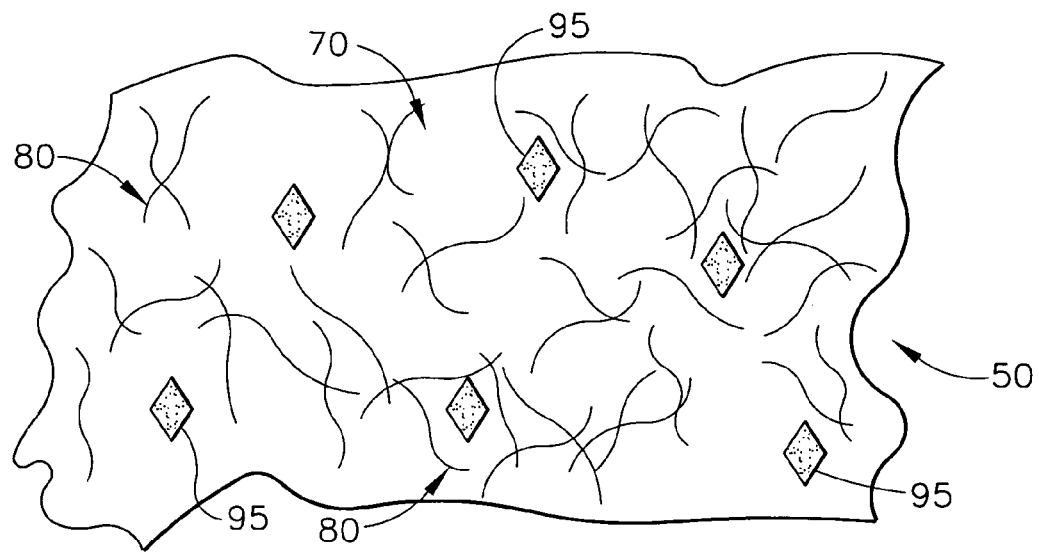
FIG. 5 is a schematic illustration of a portion of structure or coating that can be used for the medical device of FIG. 1 wherein the structure or coating has a buffering agent in accordance with the present invention.
Figure 6:
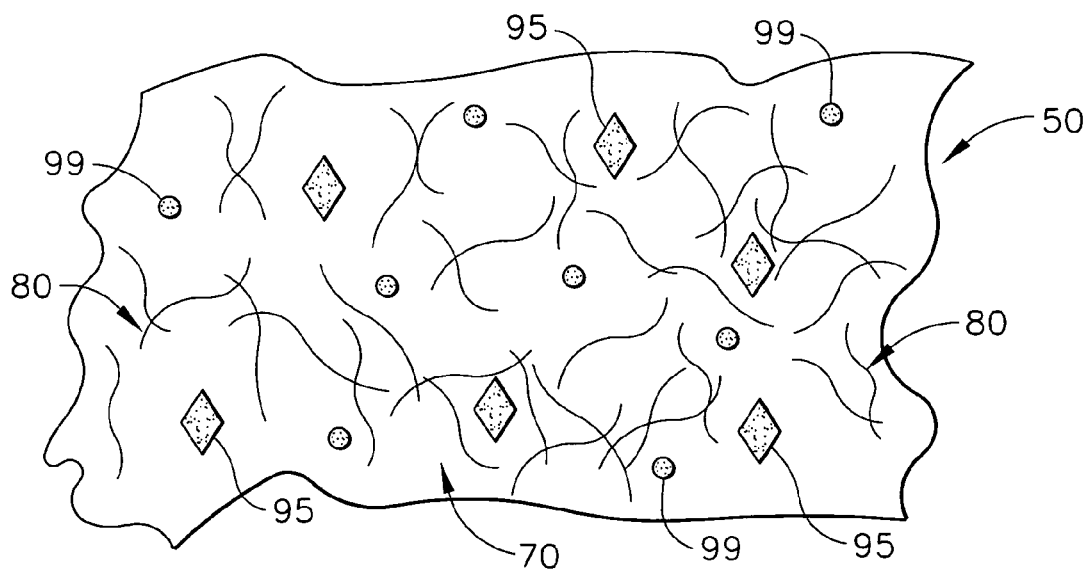
FIG. 6 is a schematic illustration of a portion of structure or coating that can be used for the medical device of FIG. 1 wherein the structure or coating has a buffering agent and a drug in accordance with the present invention.

In a two component or three component system (FIG. 5 and FIG. 6 respectively), i.e. first polymer 80, and the buffering agent 95 and optionally the drug 99 (FIG. 6), the two components or three components (including drug 99 as shown in FIG. 6) are formulated together to create an effective self-regulating system. As the first polymer material 80 breaks down, the buffering agent 95 reacts with the local acidic environment which offset the unwanted effects of acid and inflammation. If the first polymer material 80 breaks down quickly, the buffering agent 95 reacts faster (and vice-versa) to maintain a level of control on the degradation kinetics of the device 50. In the embodiments depicted in FIGS. 5 and 6, the buffering agent 95 and drug 99 (FIG. 6) is/are added in the matrix of the first bioabsorbable polymer 80 so that the buffering agent 95 is always available to react with the acidic byproducts.

As shown in FIG. 5 and FIG. 6, the medical device 50 can be prepared such that the first biodegradable and/or bioabsorbable polymer 80 has the neutralizing agent 95 on the backbone of the polymer. Thus, in this embodiment according to the present invention, the medical device 50 is a self-regulating system consisting of only two components, i.e. the first biodegradable and/or bioabsorbable polymer 80 and the neutralizing agent 95 (FIG. 5) or a self-regulating system consisting of only three components, i.e. the first biodegradable and/or bioabsorbable polymer 80, the neutralizing agent 95 and the drug 99 (FIG. 6). Accordingly, when the biodegradable and/or bioabsorbable polymer 80 degrades by hydrolysis, and the neutralizing agent 95 (chemical entity) is released (triggered by the acid formation) at the triggering time $T_t$ and will neutralize the acid and thereby raise the pH of the local environment back up to neutral, i.e. pH of about 7 as shown in FIG. 7 and preferably to pH of about 7.4 for those tissues having normal blood level pH of about 7.4. The advantage of this approach is that the acid and the neutralizing agent will be at close proximity and therefore the pH regulation can be tightly controlled. Also, the acid used to synthesize the polymer can be of a pH that is not detrimental to tissues. Moreover, as the biodegradable and/or bioabsorbable polymer 80 degrades, drug 99 is dispersed or released from the polymer 80 and device 50 thereby providing therapy to the tissue at the local environment or even systemically if desired.

A method of formulating the biomaterial structure or coating 70 of the medical device 50 using the first biodegradable and/or bioabsorbable material 80 and the second biodegradable and/or bioabsorbable material 90 and the second biodegradable and/or bioabsorbable material 90 together with the buffering agent 95 to encapsulate the buffering agent 95 is described in greater detail later below. This method is also applicable for combining with a therapeutic agent or drug 99 (represented by a solid circular shape) which can be mixed together with the polymer material of the device structure 70 (when the device 50 is made of the first biodegradable and/or bioabsorbable material 80 itself) such as shown in FIG. 3 or mixed with the buffering agent 95 and the second biodegradable and/or bioabsorbable material 90 for encapsulating both the buffering agent 90 together with the drug 99 especially when it is important to protect the stability or efficacy of the drug 99, i.e. neutralize or offset the detrimental effects of local acid environment and acidic byproducts on the structure or conformation of the drug 99.

It will be appreciated by those skilled in the art that the relative amounts of the first biodegradable and/or bioabsorbable material 80 to the second biodegradable and/or bioabsorbable material 90 and relative amounts of the buffering agent 95 and/or drug 99 to the first biodegradable and/or bioabsorbable material 80 and/or the second biodegradable and/or bioabsorbable material 90 in the composites of the present invention (represented in the embodiments depicted in FIGS. 2-6 respectively) will depend upon various parameters including, inter alia, the levels of strength, stiffness, and other physical and thermal properties, absorption and resorption rates, setting and hardening rates, deliverability, etc., which are required. The desired properties of the composites of the embodiments of the present invention and their level of requirement will depend upon the body structure area or anatomy where the medical device 50 and/or buffering agent 95 and/or drug 99 is/are needed.

The composites of the present invention can be manufactured in the following process as an example. The preformed polymers, i.e. the first biodegradable and/or bioabsorbable material 80 and the second biodegradable and/or bioabsorbable material 90 and the buffering material 95 and optionally the drug 99 and any of its required excipients are individually charged into a conventional mixing vessel having a conventional mixing device mounted therein such as an impeller i.e. the second material 90 and the buffering material 95 and drug 99 (if included) are first mixed forming encapsulated buffering material 95 and drug 99 (if included). The second biodegradable and/or bioabsorbable material polymer(s) 90 and the buffering agent 95 and optionally the drug 99 are mixed at a temperature suitable for the given polymers as is known in this field until uniformly dispersion is obtained in order to ensure that the buffering agent 95 and drug 99 when optionally included as part of the encapsulation by the second biodegradable and/or bioabsorbable polymer 90 (FIG. 4). Then, the mixture may be further processed by removing it from the mixing device, cooling to room temperature, grinding, and drying under pressures below atmospheric at elevated temperatures for a period of time. Typical encapsulation processes can be used which can include spray drying, coacervation, etc. Alternatively, encapsulation can be prepared by extruding, tray drying, drum drying or the like to form solids which are then ground to the desired particle size. The encapsulated buffering agent 95 and drug 99 (if included) is then mixed with the first biodegradable and/or bioabsorbable material 80 using suitable temperatures and processes steps such as those mentioned above and below.

The same process as outlined above is used when it is desirable to have just the first biodegradable and/or bioabsorbable material 80 as the material for the device structure or a coating 70 for the device structures (without the use of any second biodegradable and/or bioabsorbable material 90) together with the buffering agent 95 (FIG. 5) or together with the buffering agent 95 and the drug 99 (FIG. 6).

In addition to the above manufacturing method, the composites can be prepared by a one-step process by charging the buffering agent 95 and optionally the drug 99 to a reaction vessel which contains the just-formed polymers of the second biodegradable and/or bioabsorbable polymer 90 (when encapsulation is desired) or the first biodegradable and/or bioabsorbable polymer 80 (when only one biodegradable and/or bioabsorbable polymer is desired complexed together with the buffering agent 95 or the buffering agent and drug 99 such as depicted in FIG. 5 and FIG. 6 respectively).

It is important to note that all processing techniques used for the present invention will be at sufficient temperatures that will not degrade the drug 99, the buffering agent 95, the first material 80 and the second material 90.

As mentioned above, articles such as the medical devices 50 themselves may be molded from the composites of the present invention by use of various conventional injection and extrusion processes and molding equipment equipped with dry nitrogen atmospheric chamber(s) at acceptable temperatures.

The composites of this invention can be melt processed by numerous conventional methods to prepare a vast array of useful devices 50. These materials can be injection or compression molded to make implantable, biodegradable and/or bioabsorbable medical and surgical devices, especially biodegradable and/or bioabsorbable vascular devices such as stents including drug eluting stents and biodegradable and/or bioabsorbable cardiovascular devices such as heart valves including heart valves that are capable of eluting drugs 99.

Alternatively, the composites can be extruded (melt or solution) to prepare fibers and films. The filaments thus produced may be spun as multifilament yarn, or meshes, knitted or woven, and formed by conventional molding techniques into reinforced devices 50 and utilized where it is desirable that the structure have high tensile strength and desirable levels of compliance and/or ductility. Useful embodiments include preformed valves or stents for areas where vessels and heart tissue including heart valves are have been or are easily damaged or surgically removed.

As mentioned above, the composites of the present invention may also be used to coat substrates, i.e. serve as a biodegradable and/or bioabsorbable polymer coating 70 or a biodegradable and/or bioabsorbable drug eluting polymer coating 70 (FIG. 3 and FIG. 6), such as biocompatible substrates such as meshes, the various structural components and elements of medical devices, for example, the hoops, loops, flexible links or bridges or extensions of the stent 50 or the housing, flaps or other components of the heart valve 50, etc. The coatings 70 would be made by utilizing liquid composites of the present invention which would then be applied to the substrate by conventional coating techniques such as dipping, spraying, brushing, roller coating, etc.

Additionally, the composites can be molded to form films which are particularly useful for those applications where a drug delivery matrix in tissue (e.g., growth factors) is desired, for example for achieving angiogenesis and/or myogenesis in cardiovascular tissue including the vessels, myocardium, endocardium and epicardium or pericardium of the heart.

Furthermore, the composites of the present invention can be formed into foams, with open or closed cells, which are useful for applications where a high rate of tissue ingrowth is required such as remodeling heart tissue for inducing myogenesis or angiogenesis for treatment of cardiovascular disease such as congestive hear failure (CHF) or ischemic heart disease.

In more detail, the surgical and medical uses of the filaments, films, foams, molded articles, and injectable devices of the present invention include, but are not necessarily limited to vessels or heart tissue. The medical device 50 in accordance with the present invention can also be used for devices such as clamps, screws, and plates; clips; staples; hooks, buttons, and snaps; preformed tissue substitutes such as prosthetics or grafts, injectable polymers; vertebrae discs; anchoring devices such as suture anchors; septal occlusion devices; injectable defect fillers; preformed defect fillers; bone waxes; cartilage replacements; spinal fixation devices; drug delivery devices; foams with open or closed cells, and others.

Inasmuch as the foregoing specification comprises preferred embodiments of the invention, it is understood that variations and modifications may be made herein, in accordance with the inventive principles disclosed, without departing from the scope of the invention.

While preferred embodiments of the present invention have been shown and described herein, it will be obvious to those skilled in the art that such embodiments are provided by way of example only. Numerous variations, changes and substitutions will now occur to those skilled in the art without departing from the invention. Accordingly, it is intended that the invention be limited only by the spirit and scope of the appended claims.

What is claimed is:

1. A medical device for placement at a site in a patient's body and for maintaining pH levels at the site in the patient's body at neutral pH, the device comprising:
   one or more structural components made of a first biodegradable and/or bioabsorbable material which is a polymer of poly (alpha-hydroxy acid);
   a buffering agent; and
   at least one second biodegradable and/or bioabsorbable material encapsulating the buffering agent on or in the one or more structural components, said buffering agent being encapsulated by the second biodegradable and/or bioabsorbable material, the buffering agent being released from the second biodegradable and/or bioabsorbable material as the second biodegradable and/or bioabsorbable material degrades, in response to a reduction in the pH level at the site in the patient's body resulting from the hydrolysis of the first biodegradable and/or bioabsorbable material,
   wherein the device is configured so that upon exposure to an acidic environment, an amount of the second biodegradable and/or bioabsorbable material degrades and releases the encapsulated buffering agent in an amount that provides a stoichiometric balance between the amount of buffering agent released and the total amount of acid released from the device, such that the pH level is raised to a neutral pH level.

2. The medical device according to claim 1, wherein the at least one second biodegradable and/or bioabsorbable material is a surface erodible polymer.

3. The medical device according to claim 1, wherein the at least one second biodegradable and/or bioabsorbable material is a bulk erodible polymer.

4. The medical device according to claim 1, wherein the polymer of poly (alpha hydroxy acid) is aliphatic.

5. The medical device according to claim 4, wherein the aliphatic polymer is selected from the group consisting of poly (lactic acid), poly (glycolic acid), poly (caprolactone), poly (p-dioxanone) and poly (trimethylene carbonate).

6. The medical device according to claim 1, wherein the at least one second biodegradable and/or bioabsorbable material is a either a homo polymer, a copolymer or a blend of polymers.

7. The medical device according to claim 6, wherein the at least one second biodegradable and/or bioabsorbable material is a polymer selected from the group consisting of polysaccharides, poly(orthoesters), proteins, water soluble polymers and PEG based copolymers.

8. The medical device according to claim 7, wherein the at least one second absorbable material is in the form of a microparticle.

9. The medical device according to claim 7, wherein the at least one second biodegradable and/or bioabsorbable material is in the form of a nanoparticle.

10. The medical device according to claim 1, further comprising a drug encapsulated by the at least one second biodegradable and/or bioabsorbable material.

11. The medical device according to claim 1, further comprising a drug with the first biodegradable and/or bioabsorbable material.

12. The medical device according to claim 1, wherein the buffering agent is selected from the group consisting of calcium hydroxyapatite, carbonated apatite, tricalcium phosphate, calcium carbonate, sodium bicarbonate, calcium phosphate; carbonated calcium phosphates, magnesium hydroxide, amine monomers, and lactate dehydrogenase.

13. The medical device according to claim 1, wherein the buffering agent is released from the at least one second biodegradable and/or bioabsorbable material at pH <7.4.

14. The medical device according to claim 13, wherein the buffering agent is released from the at least one second biodegradable and/or bioabsorbable material at pH ranging from about 3 to about 6.

15. The medical device according to claim 14, wherein the buffering agent is released from the at least one second biodegradable and/or bioabsorbable material at pH of about 5.

16. The medical device according to claim 13, wherein the buffering agent raises pH at the site after being released from the at least one second biodegradable and/or bioabsorbable material.

17. The medical device according to claim 16, wherein the buffering agent raises pH to about 7.4 at the site after being released from the at least one second biodegradable and/or bioabsorbable material.

18. The medical device according to claim 1, wherein the device is a stent.

19. The medical device according to claim 1, wherein the device is a valve.

20. The medical device according to claim 1, wherein the device is selected from the group consisting of clamps, screws, plates, clips, staples, hooks, buttons, snaps, prosthetics, grafts, injectable polymers, vertebrae discs, anchoring devices, suture anchors, septal occlusion devices, injectable defect fillers, preformed defect fillers, bone waxes, cartilage replacements, spinal fixation devices, drug delivery devices and foams.

21. A medical device for placement at a site in a patient's body and for maintaining pH levels at the site in the patient's body at neutral pH, the device comprising;

one or more structural components having a coating thereon, the coating made of a first biodegradable and/or bioabsorbable material which is a polymer of poly (alpha-hydroxy acid);

a buffering agent; and at least one second biodegradable and/or bioabsorbable material encapsulating the buffering agent on or in the one or more structural components, said buffering agent being encapsulated by the second biodegradable and/or bioabsorbable material, the buffering agent being released from the second biodegradable and/or bioabsorbable material as the second biodegradable and/or bioabsorbable material degrades, in response to a reduction in the pH level at the site in the patient's body resulting from the hydrolysis of the first biodegradable and/or bioabsorbable material, wherein the device is configured so that upon exposure to an acidic medium an amount of the second biodegradable and/or bioabsorbable material degrades and releases the encapsulated buffering agent in an amount that provides a stoichiometric balance between the amount of buffering agent released and the total amount of acid released from the device, such that the pH level is raised to a neutral pH level.

22. The medical device according to claim 21, wherein the at least one second biodegradable and/or bioabsorbable material is a surface erodible polymer.

23. The medical device according to claim 21, wherein the at least one second biodegradable and/or bioabsorbable material is a bulk erodible polymer.

24. The medical device according to claim 21, wherein the polymer of a poly (alpha hydroxy acid) is aliphatic.

25. The medical device according to claim 24, wherein the aliphatic polymer is selected from the group consisting of poly (lactic acid), poly (glycolic acid), poly(caprolactone), poly(p-dioxanone) and poly(trimethylene carbonate).

26. The medical device according to claim 21, wherein the at least one second biodegradable and/or bioabsorbable material is a either a homopolymer, a copolymer or a blend of polymers.

27. The medical device according to claim 26, wherein the at least one second biodegradable and/or bioabsorbable material is a polymer selected from the group consisting of polysaccharides, poly(orthoesters), proteins, water soluble polymers and PEG based copolymers.

28. The medical device according to claim 27, wherein the at least one second biodegradable and/or bioabsorbable material is in the form of a microparticle.

29. The medical device according to claim 27, wherein the at least one second biodegradable and/or bioabsorbable material is in the form of a nanoparticle.

30. The medical device according to claim 21, further comprising a drug encapsulated by the at least one second biodegradable and/or bioabsorbable material.

31. The medical device according to claim 21, further comprising a drug with the first biodegradable and/or bioabsorbable material.

32. The medical device according to claim 21, wherein the buffering agent is selected from the group consisting of calcium hydroxyapatite, carbonated apatite, tricalcium phosphate, calcium carbonate, sodium bicarbonate, calcium phosphates, carbonated calcium phosphates, magnesium hydroxide, amine monomers, and lactate dehydrogenase.

33. The medical device according to claim 21, wherein the buffering agent is released from the at least one second biodegradable and/or bioabsorbable material at pH <7.4.

34. The medical device according to claim 33, wherein the buffering agent is released from the at least one second biodegradable and/or bioabsorbable material at pH ranging from about 3 to about 6.

35. The medical device according to claim 34, wherein the buffering agent is released from the at least one second biodegradable and/or bioabsorbable material at pH of about 5.

36. The medical device according to claim 33, wherein the buffering agent raises pH at the site after being released from the at least one second biodegradable and/or bioabsorbable material.

37. The medical device according to claim 36, wherein the buffering agent raises pH to about 7.4 at the site after being released from the at least one second biodegradable and/or bioabsorbable material.

38. The medical device according to claim 21, wherein the device is a stent.

39. The medical device according to claim 21, wherein the device is a valve.

40. The medical device according to claim 21, wherein the device is selected from the group consisting of clamps, screws, plates, clips, staples, hooks, buttons, snaps, prosthetics, grafts, injectable polymers, vertebrae discs, anchoring devices, suture anchors, septal occlusion devices, injectable defect fillers, preformed defect fillers, bone waxes, cartilage replacements, spinal fixation devices, drug delivery devices and foams.

41. The medical device according to claim 1, wherein a spray drying process is used to encapsulate the buffering agent within the at least one second biodegradable and/or bioabsorbable material.

42. The medical device according to claim 1, wherein a coacervation process is used to encapsulate the buffering agent within the at least one second biodegradable and/or bioabsorbable material.

43. The medical device according to claim 21, wherein a spray drying process is used to encapsulate the buffering agent within the at least one second biodegradable and/or bioabsorbable material.

44. The medical device according to claim 21, wherein a coacervation process is used to encapsulate the buffering agent within the at least one second biodegradable and/or bioabsorbable material.

* * * * *